United States Patent [19]
Tu et al.

[11] Patent Number: 6,149,647
[45] Date of Patent: Nov. 21, 2000

[54] APPARATUS AND METHODS FOR TISSUE TREATMENT

[76] Inventors: Lily Chen Tu; Hosheng Tu, both of 2151 Palermo, Tustin, Calif. 92782

[21] Appl. No.: 09/294,710

[22] Filed: Apr. 19, 1999

[51] Int. Cl.[7] .................................................. A61B 18/18
[52] U.S. Cl. ................................ 606/41; 606/37; 606/45; 607/102
[58] Field of Search ................................. 606/32, 33, 34, 606/37, 41–52; 607/98, 99, 101, 102, 115, 116

[56] References Cited

U.S. PATENT DOCUMENTS

| | | | |
|---|---|---|---|
| 5,246,438 | 9/1993 | Langberg | 606/33 |
| 5,257,635 | 11/1993 | Langberg | 607/122 |
| 5,456,662 | 10/1995 | Edwards et al. | . |
| 5,470,313 | 11/1995 | Crocker et al. | . |
| 5,545,193 | 8/1996 | Fleischman et al. | 607/99 |
| 5,582,609 | 12/1996 | Swanson et al. | 606/39 |
| 5,743,903 | 4/1998 | Stern et al. | . |
| 6,030,382 | 2/2000 | Fleishman et al. | 606/41 |

OTHER PUBLICATIONS

Eric R. Cosman et al. "Chapter 2 : Physical Aspects of Radiofrequency Energy Applications" in Huang SKS (ed.) Radiofrequency Ablation of Cardiac Arrhythmias : Basic Concepts and Clinical Applications, Armonk, NY : Futura Publishing Company Inc. 1994.

*Primary Examiner*—Linda C. M. Dvorak
*Assistant Examiner*—Roy Gibson

[57] ABSTRACT

An ablation apparatus for treating tissues of a patient, the ablation apparatus including a catheter shaft, the catheter shaft including a shaft distal section, a shaft distal end, a shaft proximal end, and at least one lumen extending between the shaft proximal end and the shaft distal end; a handle attached to the shaft proximal end, wherein the handle has a cavity; electrode means mounted at the shaft distal section for emitting energy to ablate tissue, wherein the electrode means includes a plurality of surface sections, each surface section having different surface current resistance for transmitting different electrical current density through said surface section; and RF current generating means for generating RF current for delivering to the electrode means through at least one electrical conductor, wherein the at least one electrical conductor is coupled to the electrode means.

20 Claims, 7 Drawing Sheets

APPARATUS AND METHODS FOR TISSUE TREATMENT

TECHNICAL FIELD OF THE INVENTION

The present invention generally relates to medical apparatus and methods for treating tissues. More particularly, the invention relates to ablation apparatus and ablation methods that transmit energy to electrode means having surface sections with various electrical current resistances to deliver different amount of energy to the target tissue for therapeutic purposes.

BACKGROUND OF THE INVENTION

An artery is one of the tube-shaped blood vessels that carry blood away from a heart to the body's tissues and organs. An artery is made up of an outer fibrous layer, a smooth muscle layer, a connecting tissue layer, and the inner lining cells. If arterial walls become hardened due to the accumulation of fatty substances, then blood flow can be diminished. Hardening of the arteries, or loss of vessel elasticity, is termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

Balloon angioplasty is a nonsurgical method of clearing coronary and other arteries, blocked by atherosclerotic plaque, fibrous and fatty deposits non-uniformly on the walls of arteries. A catheter with a balloon-like tip is threaded up from the arm or groin through the artery until it reaches the blocked area. The balloon is then inflated, flattening the plaque and increasing the diameter of the blood vessel opening. The arterial passage is thus widened. As a result of enlarging the hardened plaque, cracks may unfortunately occur within the plaque to expose the underlying fresh tissue or denuded cells to the blood stream.

There are limitations, however, to this technique's application, depending on the extent of the disease, the blood flow through the artery, the part of the anatomy, symmetrical orientation of the plaques, and the particular vessels involved. Plaque build-up and/or severe re-stenosis recurrence within 6 months is up to 30–40 percent of those treated. Balloon angioplasty can only be characterized as a moderate-success procedure. Recently, a newer technique of inserting a metallic stenting element is used to permanently maintain the walls of the vessel treated at its extended opening state. Vascular stents are tiny mesh tubes made of stainless steel or other metals and are used by heart surgeons to prop open the weak inner walls of diseased arteries. They are often used in conjunction with balloon angioplasty to prevent restenosis after the clogged arteries are treated. Stenting technique reduces the probability of restenosis; however, the success rate is still sub-optimal. The underlying fresh tissue or damaged cells still pose as a precursor for vessel reclosures or restenosis, regardless of stenting or not.

When a clogged artery is widened, the plaque is broken up and the underlying collagen or damaged endothelium is exposed to the blood flow. Collagen has a prothrombotic property, which is a part of the body healing process. Unless the collagen or the damaged endothelium is passivated or modulated, the chance for blood vessel clotting as well as restenosis still exists. Moderate heat is known to tighten and shrink the collagen tissue as illustrated in U.S. Pat. No. 5,456,662. Therefore, it becomes imperative to post-treat vessels walls after the walls are treated with angioplasty and/or stenting procedures. Due to asymmetrical plaque deposit circumferentially, the treatment parameters at different location shall be different.

One method of reducing the size of cellular tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment s have an advantage because of the use of a therapeutic energy that is rapidly dissipated and reduced to a non-destructive level by conduction and convection, to other natural processes.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the apparatus-to-tissue contact site to obtain the desired temperature for treating a tissue.

To effect the optimal ablation, it requires selection of the most appropriate apparatus-to-tissue contact site as well as the most effective contact surface area with appropriate energy delivery. The conventional RF ablation catheter applies one uniform RF energy to the whole electrode means. The RF energy density (or the current density expressed as amperes per unit area) is a function of the conductivity or resistivity of the current conductor circuit. More information is shown in an article entitled "Chapter 2: Physical Aspects of Radiofrequency Energy Applications" from Huang SKS, (ed.) *Radiofrequency Ablation of Cardiac Arrhythmias: Basic Concepts and Clinical Applications.* Armonk, N.Y.: Futura Publishing Company Inc. 1994. In several special indications, a certain portion of the tissue requires more RF energy delivery than other portions. This is particularly true when a large electrode is used for ablating a tumor, the tumor center requires more energy input while the peripheral regions demand less energy input. A conventional ablation catheter does not provide such capability for alternating RF energy delivery to different zones of a tissue for optimal treatment without undue damage to the surrounding tissues.

Stern et al. in U.S. Pat. No. 5,743,903 discloses a catheter including a body carrying an electrode element for emitting energy to ablate tissue, the electrode element having a predetermined operating characteristic. Said catheter includes an element retaining a prescribed identification code that uniquely identifies the predetermined operating characteristic of the electrode element. Stern et al. also discloses different types of electrodes with various add-on values of resistance. However, Stern et al. does no teach the RF current delivery to electrode means that comprises a plurality of surface sections, each surface section having different surface current conductance/resistance for transmitting different electrical current density through said surface section for optimal tissue treatment.

Therefore, there is an urgent clinical need for an improved medical apparatus having the capability to effectively deliver appropriately various amount of energy to various surface sections of a target tissue for optimal tissue treatment.

SUMMARY OF THE INVENTION

In general, it is an object of the present invention to provide a method and an improved medical ablation apparatus for generating heat, to treat the atherosclerotic vascular vessels, or other tissues/organs, such as intestine, colon, uterus, urethra tube, and the like. It is another object of the present invention to provide an ablation apparatus system having electrode means, wherein the electrode means comprises surface sections or zones with different electrical current conductance or resistance. The power density to the surface sections with different electrical current conductance is different so that the energy density at the tissue contact surface can be varied accordingly. This variation of energy density through the surface of the electrode means can be either progressive or discrete. It is still another object of the present invention to provide a method and an apparatus for monitoring the temperature of the ablated tissue, and to control the temperature by utilizing a temperature control mechanism and/or algorithm. The location of the temperature sensor means is preferably at close proximity of the electrode means of the ablation apparatus.

It is still another object of this invention to provide a method and an apparatus for treating atherosclerotic tissues, vascular walls, or tubular cellular tissues by applying RF current to the metallic members of a basket-type catheter probe system having a plurality of metallic electrodes and subsequently to the underlying tissues, wherein at least one of the plurality of preshaped expandable metallic basket members having different surface current resistance for transmitting different electrical current density through said at least one metallic basket member.

Briefly, heat is generated by supplying a suitable energy source to an apparatus, which comprises electrode means for contacting the body tissues and for emitting RF energy to the body tissues. "Electrode means" is defined in this invention as at least one metallic element having at least one electrical conductor for transmitting RF current, wherein the electrode means comprises a plurality of surface sections, each surface section has its own surface current resistance value that may be different from that of the other section(s). The electrode means may be a coil electrode, a mesh electrode, a multiple-probe electrode, a guidewire electrode, a cap electrode or a combination of the above-referred electrodes used to contact the tissues or enlarged vessels.

A suitable energy source may consist of radiofrequency energy, microwave energy, ultrasonic energy, alternating current energy, or laser energy. The energy can be applied to the electrode means and subsequently to the atherosclerotic vascular walls or cellular tissues through the electrode means. A DIP (dispersive indifferent pad) type pad or electrode that contacts the patient, is connected to the Indifferent Electrode Connector on the RF generator. Therefore, the RF current delivery becomes effective when a close circuit from a RF generator through a patient and returning to the RF generator is formed. In this invention, the electrode means may comprise a plurality of surface sections that have different surface current resistance. Therefore, a plurality of close circuits (hereby referred to as RF sub-circuits) from a RF generator through a patient and returning to the RF generator may form and energy density for each close circuit may be different. Heat is correlated to the power of the RF current delivered, to the delivery duration, and to the surface current resistance of different surface sections of the electrode means. The surface current resistance may vary progressively or discretely from one section to another section. The standard RF current generator means and its applications through the electrode means to a patient are well known for those who are skilled in the art.

In a preferred embodiment, an ablation apparatus system comprises a catheter having a catheter shaft, the catheter shaft comprising a shaft distal section, a shaft distal end, a shaft proximal end, and at least one lumen extending between the shaft proximal end and the shaft distal end. A handle is attached to the shaft proximal end, wherein the handle has a cavity. The ablation apparatus further comprises electrode means mounted at the shaft distal section for emitting energy to ablate tissue, wherein the electrode means comprises a plurality of surface sections, each surface section having different surface current resistance for transmitting different electrical current density through said surface section; and RF current generating means for generating RF current for delivering to the electrode means through at least one electrical conductor, wherein the at least one electrical conductor is coupled to the electrode means.

In one embodiment, the surface of the plurality of surface sections comprises a total surface of an electrode for the electrode means. In another embodiment, the electrode means comprises a plurality of electrodes, each surface of the plurality of surface sections comprising a total surface of each of the plurality of electrodes, wherein an electrical conductor is coupled to each electrode. In a further preferred embodiment, each surface section of the plurality of surface sections comprises an electrode material for said section having different electrical resistance. For an ablation apparatus of the present invention, each of the plurality of surface sections may comprise a surface coating for said section having different electrical resistance. Alternately, difference between electrical resistance for one surface section of the plurality of surface sections and any of the reset of the plurality of surface sections is less than 100 ohms. More preferably, the difference in resistances is less than 10 ohms. Specifically, the different surface current resistance in the present invention for transmitting different electrical current density through said surface section of the electrode means is not related to any of surface area of the electrode means, configuration of the electrode means, orientation of the electrode means, and power dispersion property of the electrode means.

In an alternate preferred embodiment, an ablation device system comprises a catheter shaft having a shaft distal section, a shaft distal end, a shaft proximal end, and at least one lumen extending between the shaft proximal end and the shaft distal end, wherein the at least one lumen has at least one opening at the shaft distal end. A handle is attached to the shaft proximal end, wherein the handle has a cavity. The ablation device further comprises an inner catheter located inside the at least one lumen of the catheter shaft, wherein the inner catheter comprises a distal end and a proximal end; electrode means mounted at about the distal end of the inner catheter for emitting energy to ablate tissue, wherein the electrode means comprises a plurality of preshaped expandable metallic basket members, each metallic basket member having a basket distal end, a basket proximal end, wherein the basket proximal ends of the preshaped expandable metallic basket members are joined at the distal end of the inner catheter and wherein the basket distal ends of the preshaped expandable metallic basket members are joined at a distal joint; at least one of the plurality of preshaped expandable metallic basket members having different surface current resistance for transmitting different electrical current density through said at least one metallic basket member; and electrode deployment mechanism mounted at the handle, wherein the electrode deployment mechanism is attached to the proximal end of the inner catheter, wherein the plurality of preshaped expandable metallic basket members is expanded at a deployed state, and wherein the plurality of preshaped expandable metallic, basket members is retracted at a non-deployed state; and a RF current generating means, wherein RF current is generated for delivering to the electrode means for therapeutic purposes.

The ablation device system may further comprise a lumen between the proximal end and the distal end of the inner catheter, and further comprise a connecting shaft inside said lumen of the inner catheter, the connecting shaft having a distal end and a proximal end, wherein the distal end of the connecting shaft is joined to the distal joint of the metallic basket members, and wherein the proximal end of the connecting shaft is coupled to the electrode deployment mechanism.

The method and medical apparatus of the present invention has several significant advantages over other known systems or techniques to treat the tissues. In particular, the apparatus system comprising electrode means having the capability of delivering various energy density to different portions of a target tissue in this invention results in a more efficient therapeutic effect, which is highly desirable in its intended application.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 7, what is shown is an embodiment of the ablation apparatus system, comprising applying radiofrequency energy therapy to treat the atherosclerotic vascular vessels or other tissues of a patient through electrode means that has the capability of delivering various energy density to different portions of a target tissue.

Figure 1:
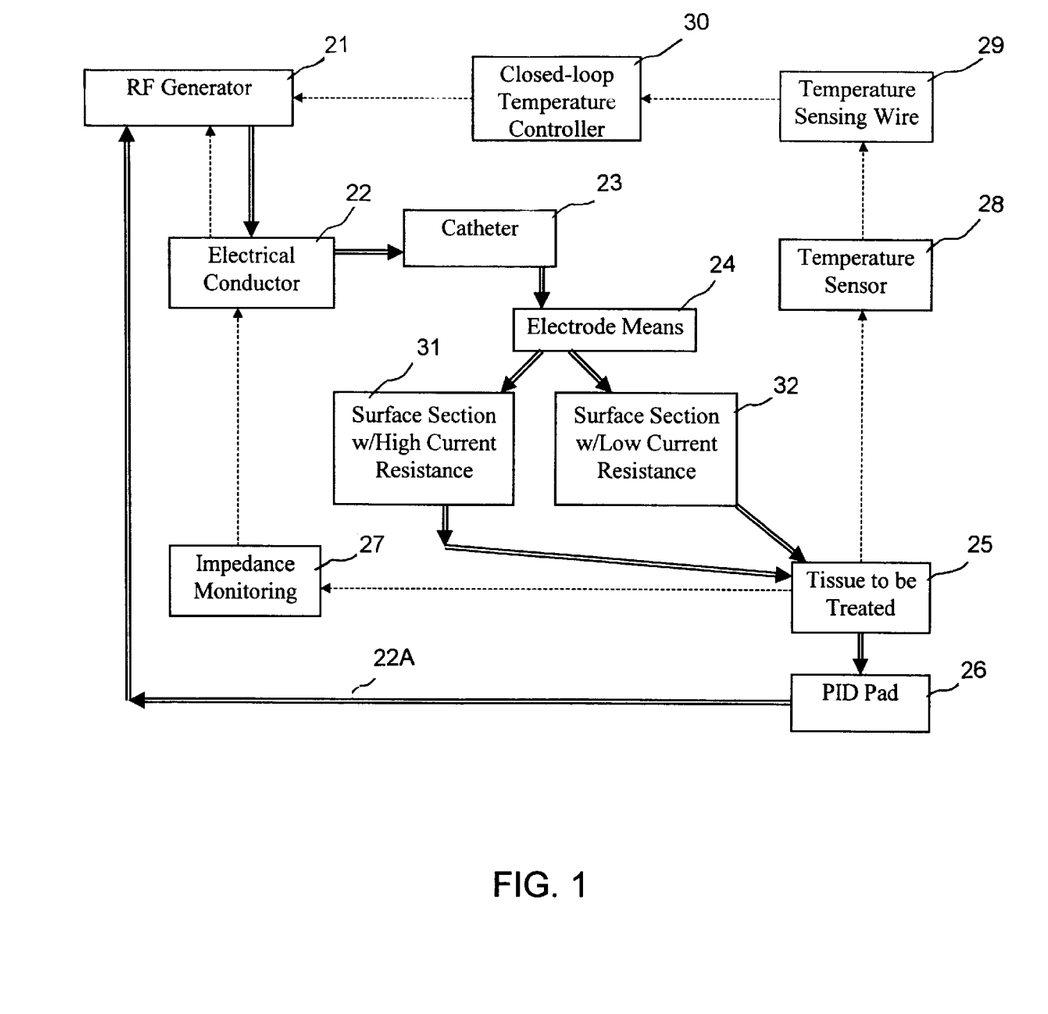
FIG. 1 is a schematic diagram of a RF treatment method in relation to the tissue through electrode means of an ablation apparatus in a patient.

FIG. 1 shows a schematic diagram of a RF treatment method in relation to the tissues through electrode means of an ablation apparatus in a patient. A RF generator 21 is connected to a catheter or an ablation apparatus 23 through an electrical conductor 22. Electrode means 24 (and 24A, 24B) of the catheter 23 is to contact the tissue 25 of a patient when the apparatus is deployed. The electrode is in close contact with the target tissue 25. A DIP (dispersive indifferent pad) type electrode 26 that contacts a patient is connected to the Indifferent Electrode Connector on the RF generator 21. Therefore, the RF current delivery becomes effective when a close circuit from a RF generator through a patient and returning to the RF generator through a second electrical conductor 22A is formed.

Impedance 27 measured from the tissue contact is to ensure good tissue contact for ablation, otherwise the RF current is cutoff when the impedance is unreasonably high. A temperature sensor 28 is used to measure the tissue temperature and is relayed through a temperature sensing wire 29 and a closed-loop temperature controlled 30 for controlling the ablative energy delivered. Heat is controlled by the power of the RF current delivered, by the delivery duration, and other factors such as predetermined surface resistance.

Electrode means 24 is mounted at the shaft distal section for emitting energy to ablate tissue, wherein the electrode means 24 comprises a plurality of surface sections 31, 32; each surface section has different surface current resistance for transmitting different electrical current density through said surface section 31, 32. The close circuit for RF energy delivery in the present invention may comprise a plurality of sub-circuits. The variation of the surface resistance of the electrode means 24 may be progressively, discretely, or separated by an insulating boundary layer.

Figure 2:
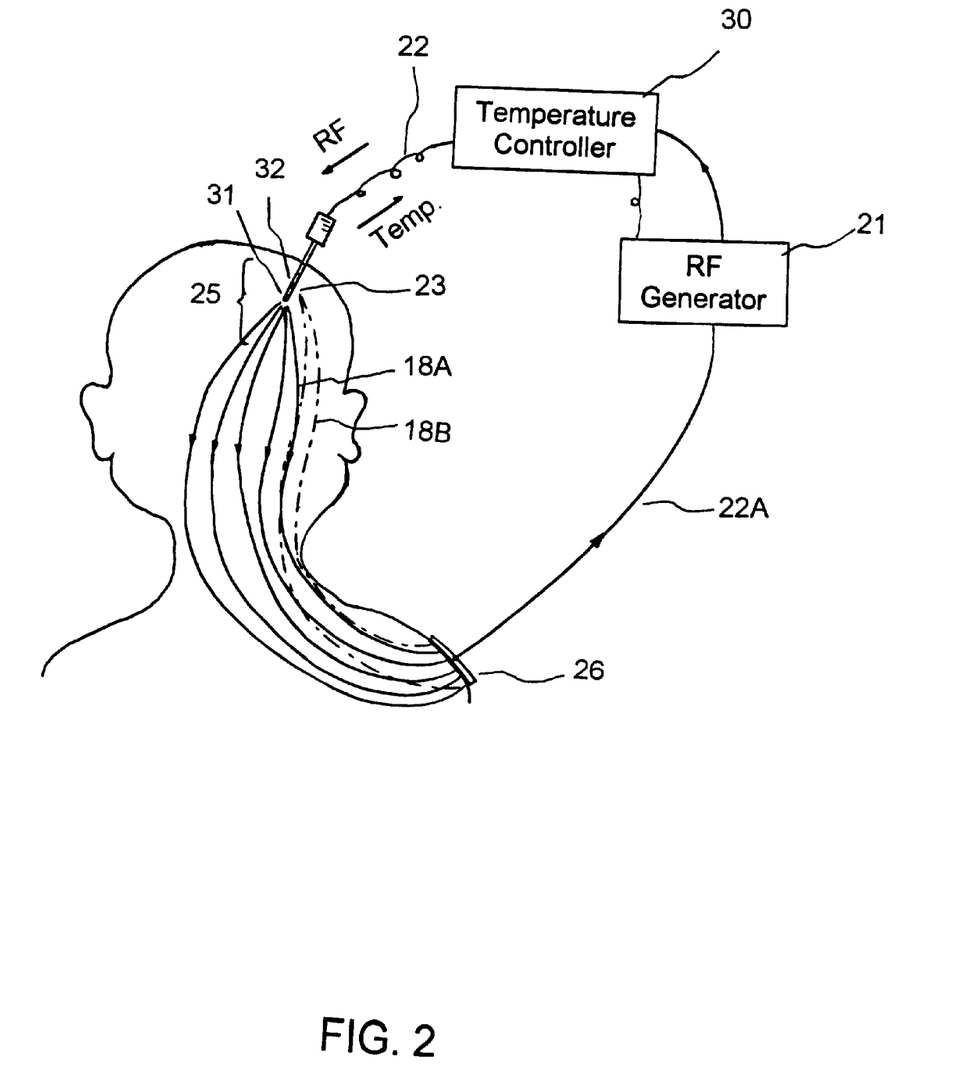
FIG. 2 is an illustrative diagram of RF energy transmission through electrode means of the present invention.

FIG. 2 shows an illustrative diagram of RF energy transmission through electrode means of the present invention, including a plurality of RF sub-circuits 18A, 18B in a discrete form. When an ablation apparatus 23 is placed against a target tissue 25, the electrode means 24 may comprises a plurality of surface sections 31, 32 having different surface resistance and different energy density. One RF sub-circuit 18A relay RF current from the surface section 31 to the indifferent electrode 26 while the other RF sub-circuit 18B relays RF current from the surface section 32 to the indifferent electrode 26. The returning electrical conductor 22A to the RF generator 21 forms a complete RF circuit, which comprises a plurality of sub-circuits. The energy delivered at the tissue contact site of the surface sections 31 and 32 is different and is a function of the power applied, the electrical current resistance, among other factors.

Figure 3:
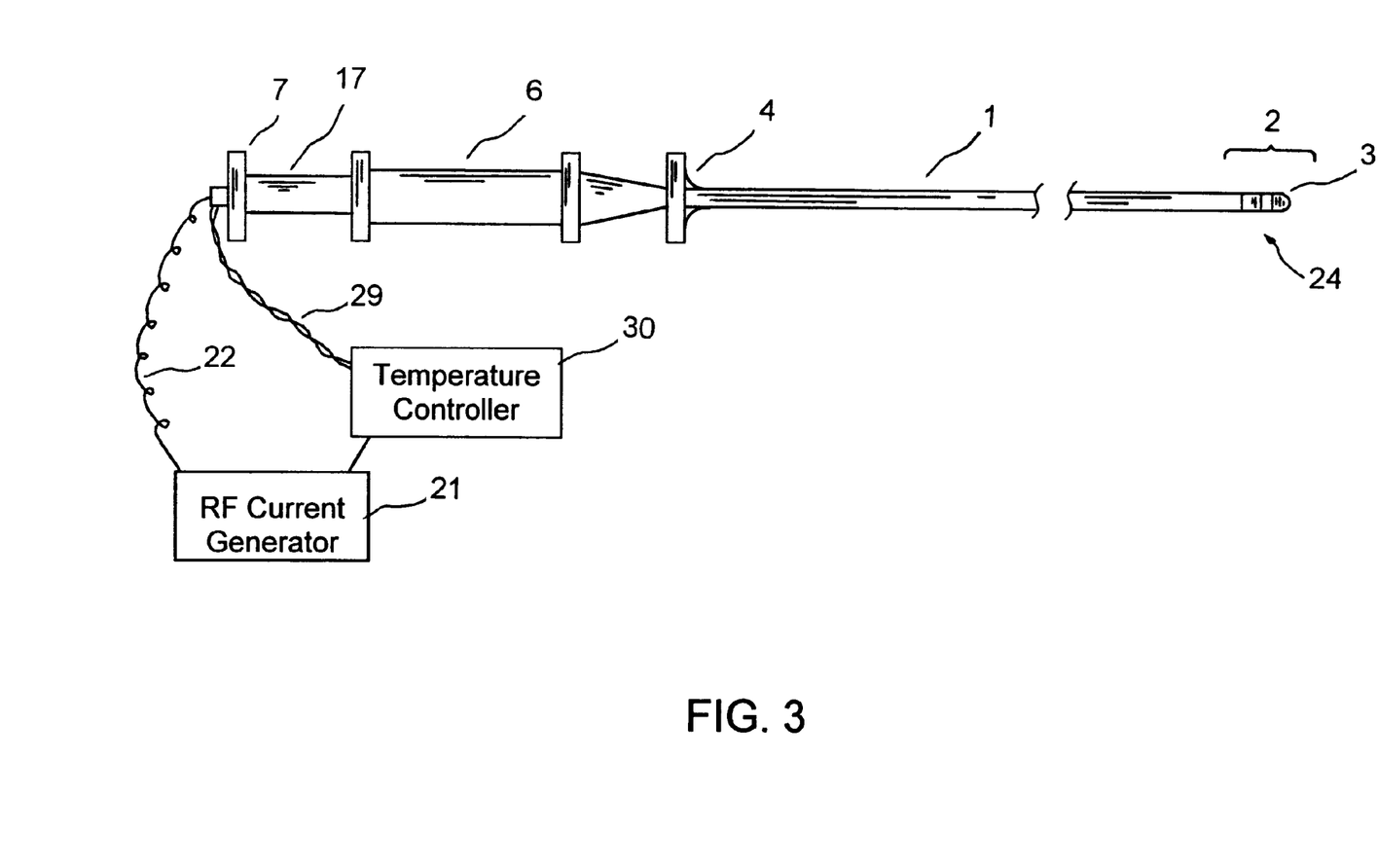
FIG. 3 is an overall view of the ablation apparatus system having electrode means and a RF current generator, constructed in accordance to the principles of the present invention.

FIG. 3 shows an overall view of the ablation apparatus system having electrode means and a RF current generator, constructed in accordance with the principles of the preset invention. An ablation apparatus system comprises a catheter 23 having a catheter shaft 1, the catheter shaft 1 comprising a shaft distal section 2, a shaft distal end 3, a shaft proximal end 4, and at least one lumen 5 extending between the shaft proximal end 4 and the shaft distal end 3. A handle 6 is attached to the shaft proximal end 4, wherein the handle has a cavity. The catheter further comprises electrode means 24 mounted at the shaft distal section 2 for emitting energy to ablate tissue, wherein the electrode means 24 comprises a plurality of surface sections 31, 32, 31A, 32A, 31B, 32B, 31C, 32C, 31D, 32D, each surface section having different or varying surface current resistance for transmitting different or varying electrical current density through said surface section. In this invention, the "different surface current resistance" means discretely different; while the "varying surface current resistance" means progressively varying. The apparatus system comprises RF current generating means 21 for generating RF current for delivering to the electrode means 24 through at least one electrical conductor 22, wherein the at least one electrical conductor is coupled to the electrode means 24.

Figure 4A:
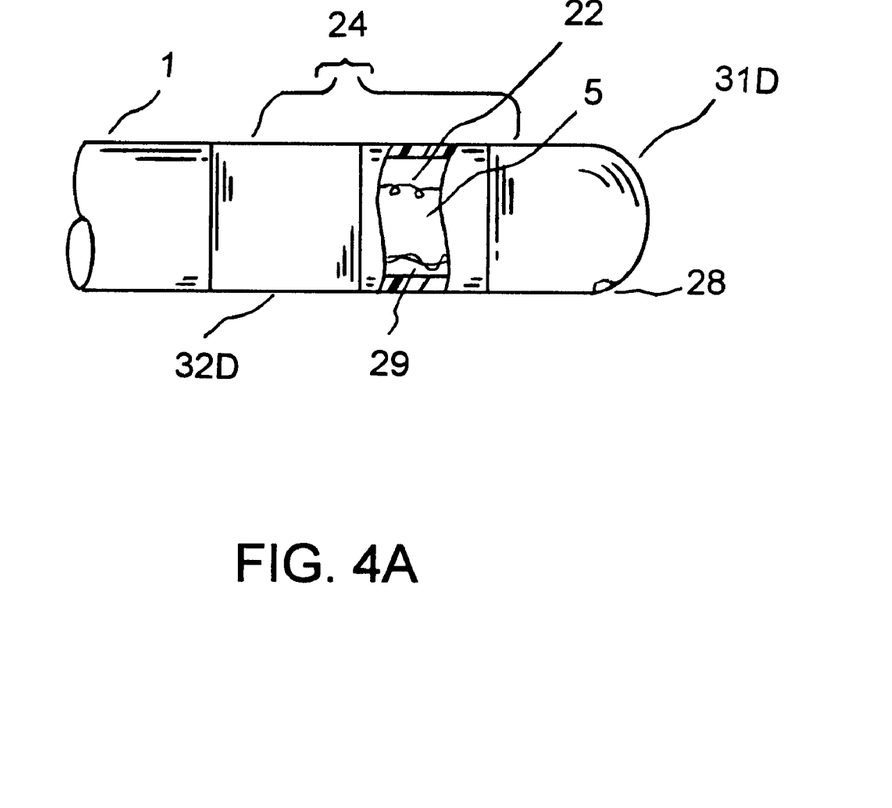
FIG. 4A is a detailed view of the distal end portion of a preferred apparatus, wherein the electrode means has a plurality of surface sections, each surface section having different surface current resistance for transmitting different electrical current density through said surface section.

FIG. 4A shows a detailed view of the distal end portion of a preferred apparatus, wherein the electrode means has a plurality of surface sections on separate electrodes, each surface section having different surface current resistance for transmitting different electrical current density through said surface section. The electrode means 24 comprises a plurality of electrodes 31D, 32D, each surface of the plurality of surface sections comprising a total surface of each of the plurality of electrodes, wherein an electrical conductor is coupled to each electrode 31D, 32D. Each surface section of the plurality of surface sections may comprise an electrode material for said section having different electrical resistance, such as platinum for electrode 31D and gold for electrode 32D. Alternately, each of the plurality of surface sections may comprise a surface coating for said section having different electrical resistance, such as platinum surface coating for electrode 31D and gold surface coating for electrode 32D.

Figure 4B:
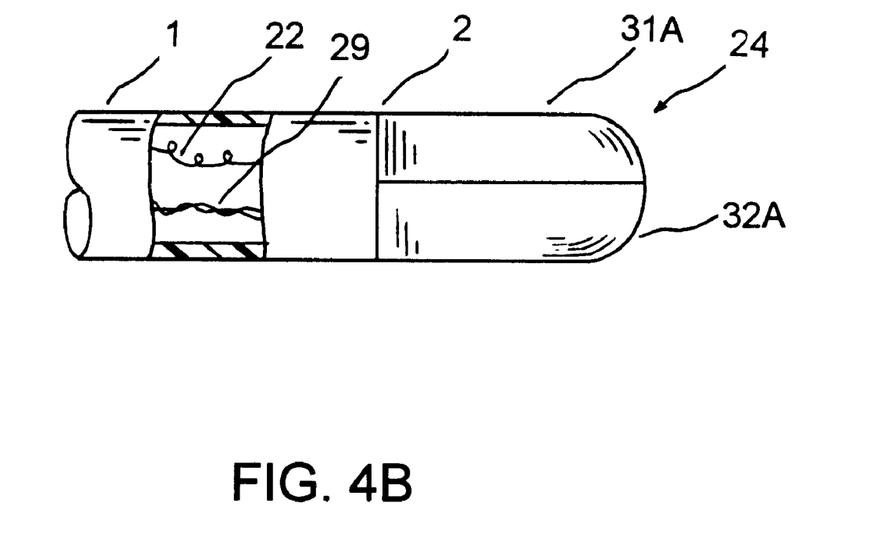
FIG. 4B is a detailed view of the distal end portion of another preferred apparatus, wherein the electrode means has a plurality of surface sections on one electrode, each surface section having different surface current resistance for transmitting different electrical current density through said surface section.

Similarly, FIG. 4B shows a detailed view of the distal end portion of another preferred apparatus, wherein surface of the plurality of surface sections comprises a total surface of an electrode 31A and 32A for the electrode means 24 on one electrode. Each surface section of the plurality of surface sections may comprise an electrode material for said section having different electrical resistance, such as platinum for electrode portion 31A and gold for electrode portion 32A. Alternately, each of the plurality of surface sections may comprise a surface coating for said section having different electrical resistance, such as platinum surface coating for electrode portion 31A and gold surface coating for electrode portion 32A.

Figure 5:
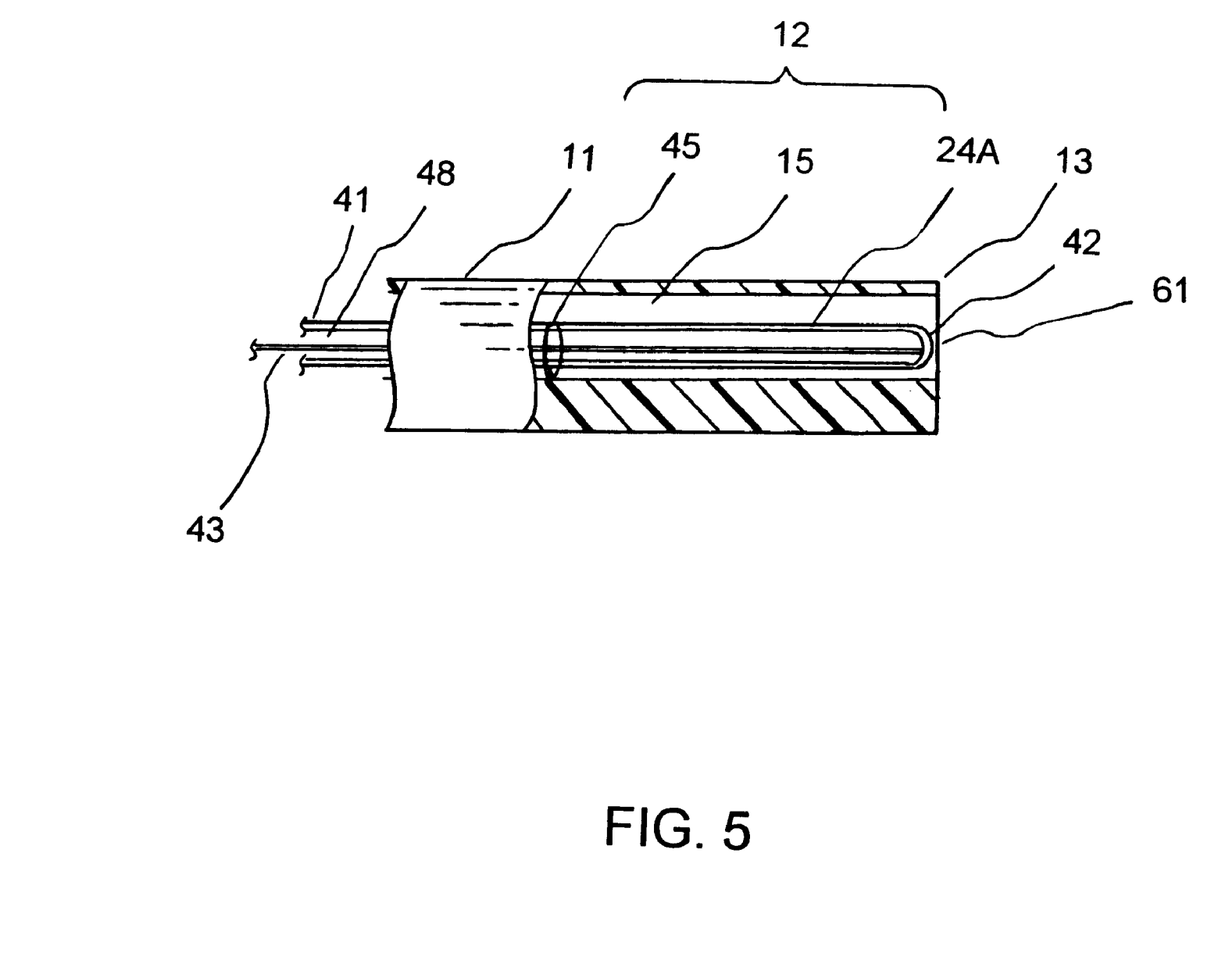
FIG. 5 is a cross-sectional view of the distal end portion of an alternate apparatus, the apparatus having a deployable electrode means positioned within the lumen of an inner catheter at a non-deployed state.

As shown in FIG. 5, a preferred ablation apparatus system comprises a catheter 23 having a catheter shaft 11, the catheter shaft having a shaft distal section 12, a shaft distal end 13, a shaft proximal end, and at least one lumen 15 extending between the shaft proximal end and the shaft distal end 13, wherein the at least one lumen 15 has optionally at least one opening 61 at the shaft distal end 13.

An inner catheter 41 is located inside the at least one lumen 15 of the catheter shaft 11, wherein the inner catheter 41 comprises a distal end 45 and a proximal end. An electrode means 24A is mounted at the distal end 45 of the inner catheter 41, wherein the electrode means 24A comprises a plurality of preshaped expandable metallic basket members 31B, 32B, each metallic basket member having a basket distal end, a basket proximal end, wherein the basket proximal ends of the expandable metallic basket members are joined at the distal end 45 of the inner catheter 41 and wherein the basket distal ends of the expandable metallic basket members are joined at a distal joint 42.

An electrode deployment mechanism 17 is mounted on the handle 6, wherein the electrode deployment mechanism 17 is attached to the proximal end of the inner catheter 41, wherein the plurality of preshaped expandable metallic basket members is expanded at a deployed state, and wherein the plurality of preshaped expandable metallic basket members is retracted at a non-deployed state. The ablation apparatus system comprises a RF current generating means 21, wherein the RF current is supplied to the electrode means 24A for therapeutic purposes.

Figure 6:
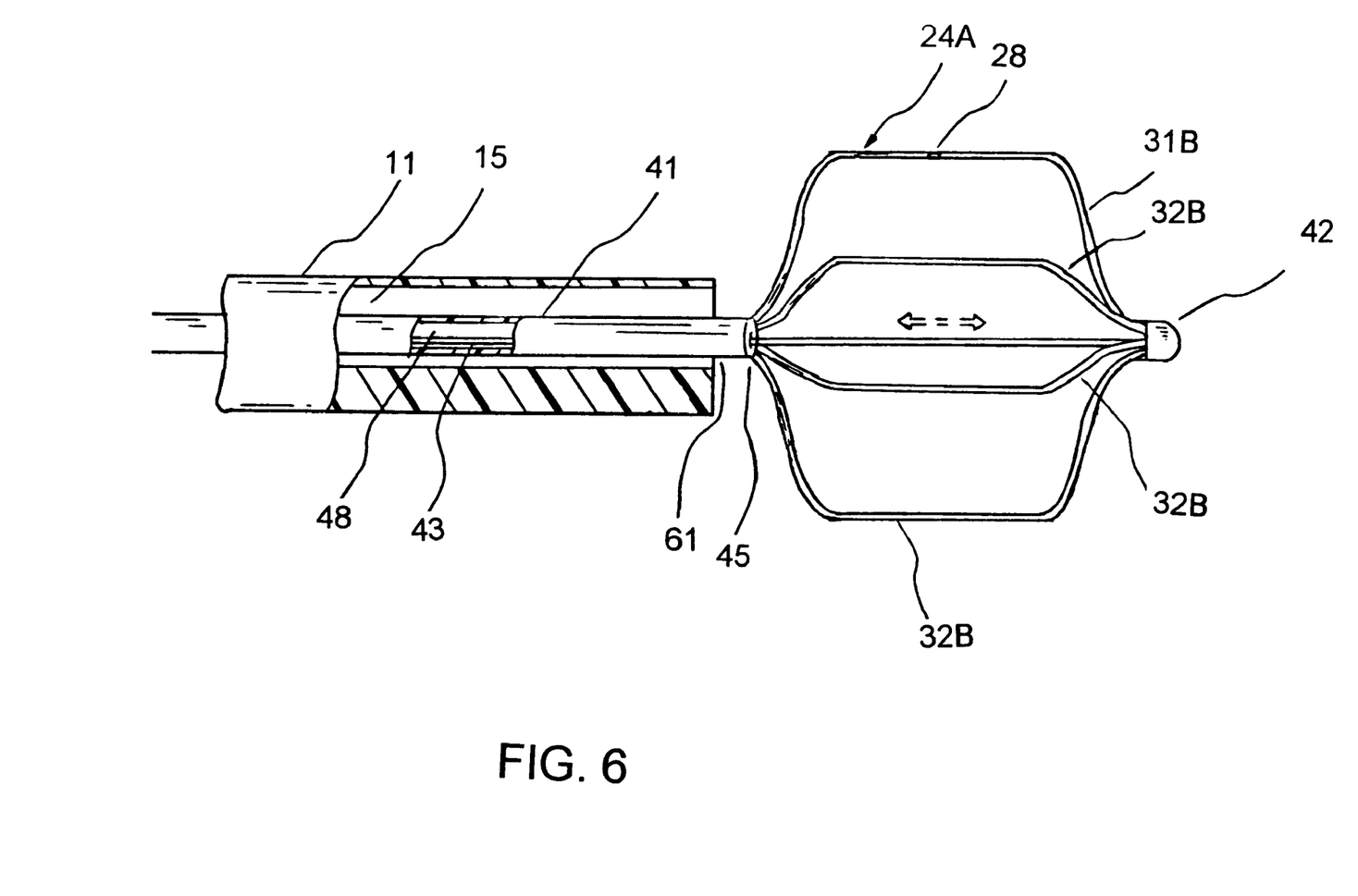
FIG. 6 is a cross-sectional view of the distal end portion of the alternate apparatus, the apparatus having a deployable electrode means comprising a plurality of preshaped expandable metallic basket members at a deployed state.

FIG. 6 shows a cross-sectional view of the distal end portion 12 of the apparatus, wherein the apparatus has a deployable electrode means 24A positioned within the lumen 15 of the catheter shaft 11 at a non-deployed state.

The ablation apparatus system may further comprise a lumen 48 between the proximal end and the distal end 45 of the inner catheter 41, and further comprises a connecting shaft 43 inside said lumen 48 of the inner catheter 41. The connecting shaft 43 has a distal end and a proximal end, wherein the distal end of the connecting shaft 43 is joined to the distal joint 42 of the metallic basket members, and wherein the proximal end of the connecting shaft is secured to the electrode deployment mechanism 17. A special optionally push-pull controller 7 on the handle adapted for the push-pull operation of the connecting shaft 43 may be part of the electrode deployment mechanism 17.

An insulated electrical conductor 22 or the inner catheter itself as a conducting means passes through the lumen 15 of the catheter shaft 11 and is connected to the electrode means 24A. The other end of the electrical conductor means is connected to an external RF generator 21.

In a preferred embodiment, at least one 31B of the plurality of preshaped expandable metallic basket members 31B, 32B having different surface current resistance than that of the other members 32B for transmitting different electrical current density through said at least one metallic basket member.

Figure 7:
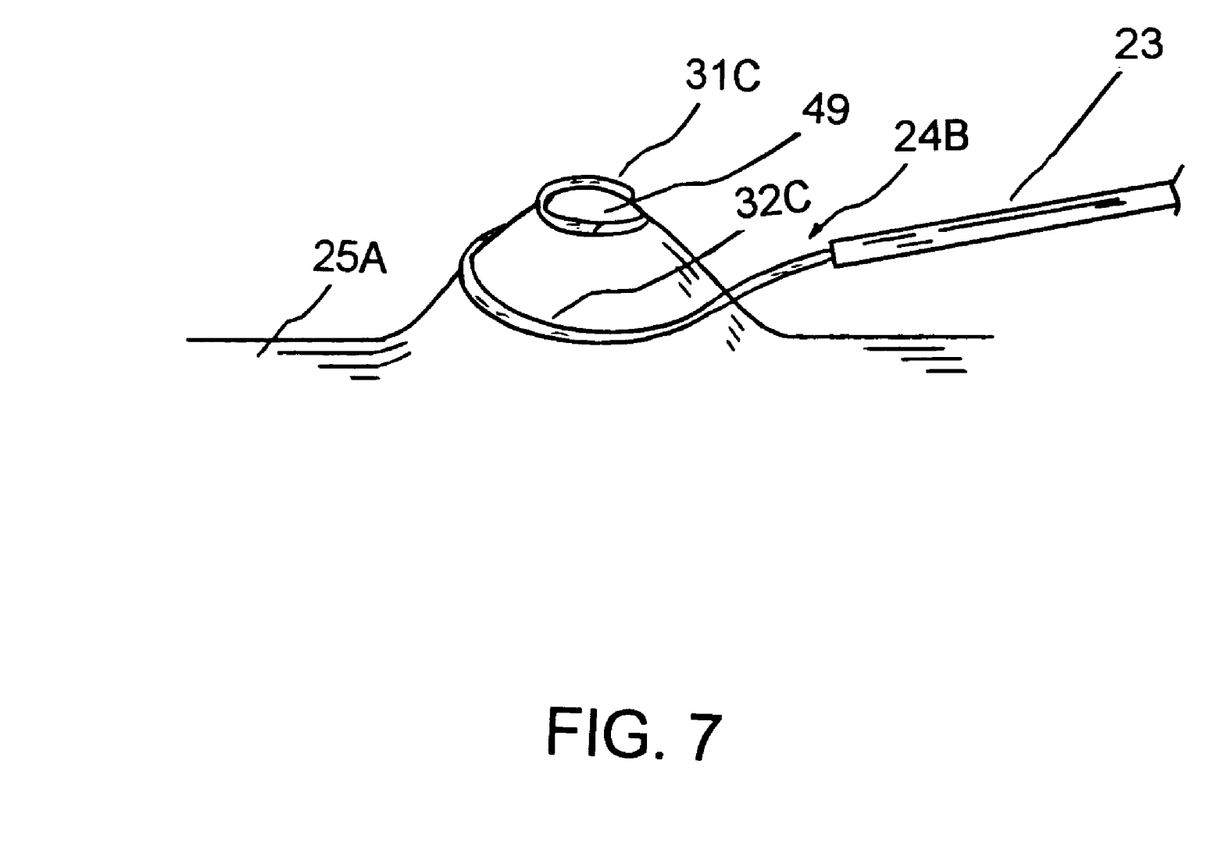
FIG. 7 is a perspective view of the tissue treatment using a coil-type electrode means of the present invention on a tumor.

In one embodiment, at least one temperature sensing means 28 is disposed at close proximity of the electrode means 24, 24A, or 24B. Insulated temperature sensor wire means 29 passes from the temperature sensing means 28, to an external temperature control mechanism 30 through an outlet connector on the handle. The RF current delivery may be controlled by using the measured temperature from the temperature sensing means 28, through a closed-loop temperature control mechanism 30. When the measured temperature rises to a preset high-limit point, the temperature control mechanism sends out a signal to cut off the RF current supply or switch to the surface section having higher current resistance characteristic. In a similar manner, when the measured temperature drops to a preset low-limit point, the temperature control mechanism sends out a signal to activate the RF current supply or switch to the surface section having lower current resistance characteristic.

A method for tissue treatment using an ablation apparatus system, the ablation apparatus system comprises a catheter having electrode means mounted at a shaft distal section for emitting energy to ablate tissue, wherein the electrode means comprises a plurality of surface sections, each surface section having different surface current resistance for transmitting different electrical density through said surface section; and RF current generating means for generating RF current for delivering to the electrode means through at least one electrical conductor, wherein the at least one electrical conductor is coupled to the electrode means. The method comprises the steps of: (a) inserting the ablation apparatus through a natural opening or a conduit to the location of the tissue to be treated; (b) deploying the electrode means to contact tissue; and (c) applying RF current to the electrode means to effect treatment of the tissues for therapeutic purposes. The method may further comprise contacting the electrode means to at least one implanted stent for delivering RF energy to tissue through the at least one implanted stent.

A method for treating atherosclerotic tissues of a patient using an ablation apparatus system is illustrated. The ablation apparatus system comprises a catheter shaft 11 and an inner catheter 21, the inner catheter having a proximal end, a distal end and a deployable electrode means 4 mounted at the distal end of the inner catheter, wherein the electrode means comprises a plurality of preshaped expandable metallic basket members, each metallic basket member having a basket distal end, a basket proximal end, wherein the basket proximal ends of the metallic basket members are joined at the distal end of the inner catheter and wherein the basket distal ends of the metallic basket members are joined at a distal joint. The apparatus system further comprises a RF current generating means, wherein the RF current is supplied to the electrode means. The method comprises the steps of: (a) inserting the ablation apparatus through an artery or a vein to the location of the atherosclerotic tissues; (b) deploying the electrode means to expand the preshaped expandable metallic basket members adapted to contact the atherosclerotic tissues; and (c) applying RF current to the electrode means to effect treatment of the atherosclerotic tissues.

FIG. 7 shows a perspective view of the tissue treatment using a coil-type electrode means 24B of the present invention on a tumor 49. The electrode means 24B comprises a coil electrode, wherein the coil electrode has a plurality of surface sections 31C, 32C. Each section 31C, 32C has different surface electrical current resistance. For illustration purposes, the section 31C with lower current resistance is placed on the top of the tumor 49 where more therapeutic energy density may be required. In the meantime, the section 32C with higher current resistance is placed on the peripheral regions of the tumor 49 where less therapeutic energy density may be needed. By controlling the appropriate energy delivery to different sections either progressively or discretely, the tumor can be treated without undue thermal damage to the surrounding tissue 25A.

The radiofrequency energy current in this invention is preferably within the range of 50 to 2,000 kHz. In a particular embodiment, the material for the electrode means of this invention consists of conductive metals such as platinum, iridium, gold, silver, stainless steel, tungsten, Nitinol, or an alloy of these metals.

The difference between electrical resistance for one surface section of the plurality of surface sections and any of the rest of the plurality of surface sections is less than 100 ohms, preferably less than 10 ohms. In the ablation apparatus system of the present invention, the different surface current resistance for transmitting different electrical current density through said surface section of the electrode means is not related to any of surface area of the electrode means, configuration of the electrode means, orientation of the electrode means, and power dispersion property of the electrode means.

Energy density, expressed in terms of watts/cm$^2$, is a product of (Voltage)$^2$ divided by (resistance per Unit Area) of the electrode surface, wherein the Voltage is the electromotive force across the electrode surface of the electrode means. Relatively, the higher the Resistance per Unit Area, the lower the energy density through the electrode surface.

From the foregoing description, it should now be appreciated that an ablation apparatus system for the tubular organs, atherosclerotic tissues, and the treatment of vascular tissues, comprising a suitable controllable energy source or energy density has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. An ablation apparatus system comprising:
    a catheter having a catheter shaft, the catheter shaft comprising a shaft distal section, a shaft distal end, a shaft proximal end, and at least one lumen extending between the shaft proximal end and the shaft distal end;
    a handle attached to the shaft proximal end, wherein the handle has a cavity;
    electrode means mounted at the shaft distal section for emitting energy to ablate tissue, wherein the electrode means comprises a plurality of surface sections, each surface section having different or varying surface current resistance for transmitting different or varying electrical current density through said surface section; and
    RF current generating means for generating RF current for delivering to the electrode means through at least one electrical conductor, wherein the at least one electrical conductor is coupled to the electrode means.

2. The ablation apparatus system as in claim 1, wherein surface of the plurality of surface sections comprises a total surface of an electrode for the electrode means.

3. The ablation apparatus system as in claim 1, wherein the electrode means comprises a plurality of electrodes, each surface of the plurality of surface sections comprising a total surface of each of the plurality of electrodes, wherein an electrical conductor is coupled to each electrode.

4. The ablation apparatus system as in claim 1, wherein the electrode means is selected from the group consisting of a coil electrode, a mesh electrode, a multiple-probe electrode, a guidewire electrode, a cap electrode and combination of the above-referred electrodes.

5. The ablation apparatus system as in claim 1, wherein each surface section of the plurality of surface sections comprises an electrode material for said section having different or varying electrical resistance.

6. The ablation apparatus system as in claim 1, wherein each of the plurality of surface sections comprises a surface coating for said section having different or varying electrical resistance.

7. The ablation apparatus system as in claim 1, wherein difference between electrical resistance for one surface section of the plurality of surface sections and any of the rest of the plurality of surface sections is less than 100 ohms.

8. The ablation apparatus system as in claim 1, wherein the different surface current resistance for transmitting different electrical current density through said surface section of the electrode means is not related to any of surface area of the electrode means, configuration of the electrode means, orientation of the electrode means, and power dispersion property of the electrode means.

9. The ablation apparatus system as in claim 1 further comprising at least one temperature sensor, wherein the at least one temperature sensor is disposed at close proximity of the electrode means.

10. The ablation apparatus system as in claim 9 further comprising a temperature controller, wherein temperature measured from the at least one temperature sensor is relayed to the temperature controller and is adapted to effect the RF current delivery to the electrode means.

11. The ablation apparatus system of claim 1, wherein the RF current is within the range of 50 to 2,000 kHz.

12. The ablation apparatus system of claim 1, wherein material for the electrode means is selected from the group consisting of platinum, iridium, gold, silver, stainless steel, Nitinol, tungsten, and an alloy of their mixtures.

13. An ablation device system comprising:
- a catheter shaft having a shaft distal section, a shaft distal end, a shaft proximal end, and at least one lumen extending between the shaft proximal end and the shaft distal end, wherein the at least one lumen has at least one opening at the shaft distal end;
- a handle attached to the shaft proximal end, wherein the handle has a cavity;
- an inner catheter located inside the at least one lumen of the catheter shaft, wherein the inner catheter comprises a distal end and a proximal end;
- electrode means mounted at about the distal end of the inner catheter for emitting energy to ablate tissue, wherein the electrode means comprises a plurality of preshaped expandable metallic basket members, each metallic basket member having a basket distal end, a basket proximal end, wherein the basket proximal ends of the preshaped expandable metallic basket members are joined at the distal end of the inner catheter and wherein the basket distal ends of the preshaped expandable metallic basket members are joined at a distal joint;
- at least one of the plurality of preshaped expandable metallic basket members having different surface current resistance for transmitting different electrical current density through said at least one metallic basket member,
- an electrode deployment mechanism mounted at the handle, wherein the electrode deployment mechanism is attached to the proximal end of the inner catheter, wherein the plurality of preshaped expandable metallic basket members is expanded at a deployed state, and wherein the plurality of preshaped expandable metallic basket members is retracted at a non-deployed state; and
- a RF current generating means, wherein RF current is generated for delivering to the electrode means for therapeutic purposes.

14. The ablation device system as in claim 13 further comprising a lumen between the proximal end and the distal end of the inner catheter, and further comprising a connecting shaft inside said lumen of the inner catheter, the connecting shaft having a distal end and a proximal end, wherein the distal end of the connecting shaft is joined to the distal joint of the metallic basket members, and wherein the proximal end of the connecting shaft is coupled to the electrode deployment mechanism.

15. The ablation device system as in claim 13 further comprising at least one temperature sensor, wherein the at least one temperature sensor is disposed at close proximity of the electrode means.

16. The ablation apparatus system as in claim 13, wherein the at least one of the plurality of preshaped expandable metallic basket members having different surface current resistance for transmitting different electrical current density through said at least one metallic basket member comprises a surface coating for said at least one metallic basket member having different surface current resistance.

17. A method for tissue treatment using an ablation apparatus system, the ablation apparatus system comprising a catheter having a catheter shaft, the catheter shaft comprising a shaft distal section, a shaft distal end, a shaft proximal end, and at least one lumen extending between the shaft proximal end and the shaft distal end; a handle attached to the shaft proximal end, wherein the handle has a cavity; electrode means mounted at the shaft distal section for emitting energy to ablate tissue, wherein the electrode means comprises a plurality of surface sections, each surface section having different or varying surface current resistance for transmitting different or varying electrical current density through said surface section; and RF current generating means for generating RF current for delivering to the electrode means through at least one electrical conductor, wherein the at least one electrical conductor is coupled to the electrode means;

the method comprising the steps of:
(a) inserting the ablation apparatus through a natural opening or a conduit to the location of the tissue to be treated;
(b) deploying the electrode means to contact tissue; and
(c) applying RF current to the electrode means to effect treatment of the tissues for therapeutic purposes.

18. A method for tissue treatment as in claim 17, the method further comprising contacting the electrode means to at least one implanted sent for delivering RF energy to tissue through the at least one implanted stent.

19. A method for tissue treatment as in claim 18, wherein the tissue is intravascular luminal tissue.

20. A method for tissue treatment as in claim 17, the method further comprising the ablation apparatus having at least one temperature sensor, wherein the at least one temperature sensor is disposed at close proximity of the electrode means.

* * * * *